United States Patent

Hum et al.

[11] Patent Number: 5,805,658
[45] Date of Patent: Sep. 8, 1998

[54] METHODS AND APPARATUS FOR DETECTING GANTRY INTERFERENCE IN A COMPUTED TOMOGRAPHY SYSTEM

[75] Inventors: Russell Wayne Hum, Waukesha; Thomas Robert Murray, Delafied; Christopher J. Falkner, Waukesha, all of Wis.

[73] Assignee: General Electric Company, Schenectady, N.Y.

[21] Appl. No.: 774,575

[22] Filed: Dec. 31, 1996

[51] Int. Cl.⁶ .................................... H05G 1/54
[52] U.S. Cl. .................. 378/4; 378/8; 378/95; 378/117
[58] Field of Search ............ 378/4, 8, 95, 114, 378/117

[56] References Cited

U.S. PATENT DOCUMENTS

| | | | |
|---|---|---|---|
| 5,097,495 | 3/1992 | Gray et al. | 378/117 |
| 5,105,455 | 4/1992 | Kato et al. | 378/117 |
| 5,651,044 | 7/1997 | Klotz, Jr. et al. | 378/117 |

*Primary Examiner*—David P. Porta
*Attorney, Agent, or Firm*—John S. Beulick; John H. Pilarski

[57] ABSTRACT

The present invention, in one embodiment, is an interference detection assembly for detecting patient and patient table interference with a gantry of a computed tomography system. The assembly, in one form, includes a frusto-conical capacitive plate secured to a leading frusto-conical surface of the gantry bore. The capacitive plate is coupled to a control unit which detects changes in the capacitance of the capacitive plate. When the plate is discharged below a threshold charge, the control unit generates a signal which may be used to automatically interrupt a scan.

15 Claims, 2 Drawing Sheets

METHODS AND APPARATUS FOR DETECTING GANTRY INTERFERENCE IN A COMPUTED TOMOGRAPHY SYSTEM

FIELD OF THE INVENTION

This invention relates generally to computed tomography (CT) imaging and more particularly, to detecting patient and patient table interference with a gantry in computed tomography systems.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

The gantry typically is coupled to a patient table and includes two ends and a gantry bore extending between the ends. The gantry bore includes a leading frusto-conical section tapering to a substantially cylindrical section, and is sized to receive a patient and patient table. The system is configured to translate the table (and the patient) through the gantry bore. Preferably, the gantry bore and the patient table are substantially aligned so that the patient and patient table translate through the gantry bore without interfering with the gantry, i.e., contacting the gantry bore perimeter.

While performing a patient scan, it may be desirable to tilt the gantry to obtain different views. When tilting the gantry, however, the patient or the patient table may physically contact the perimeter of the gantry bore, or "interfere" with the gantry. Typically, such contact occurs at the perimeter of the leading frusto-conical section, but such contact may occur anywhere along the gantry bore. It obviously is desirable to detect such interference and to halt further gantry tilt and table translation as soon as such interference occurs.

In the past, and due to the importance of preventing physical contact between the patient and the gantry, the operator manually adjusts the gantry to the desired tilt prior to scanning. To detect patient and patient table interference with the gantry during a scan, CT systems typically include tape switches or pneumatic pressure sensors secured to the perimeter of the leading frusto-conical section.

While generally acceptable, tape switches and pneumatic pressure sensors are difficult to secure to the frusto-conical gantry bore surface and are difficult to clean. Specifically, and as a result of physical contact, tape switches and pneumatic pressure sensors sometimes are dislodged or otherwise damaged. Moreover, a plurality of such switches and sensors are necessary for adequate interference detection. To be effective, tape switches and pneumatic sensors typically are secured to the gantry along a line or plane, and many strings of such sensors extending radially from the gantry bore center axis are required to effectively detect interference.

Rather than tape switches and pneumatic pressure sensors, some CT systems include optical sensors for detecting interference with the gantry. The accuracy of known optical sensors typically is less than desired since known optical sensors sometimes detect false, or phantom, interference with the gantry. In addition, as with tape switches and pneumatic pressure sensors, many strings of optical sensors extending radially from the gantry bore center axis are required to effectively detect interference.

With respect to the above-described sensors, and for aesthetic purposes and accuracy, it is important to keep the sensors clean. Cleaning such known switches, particularly switches secured to the gantry by tape, can be a time consuming and cumbersome process. Further, if it is not possible to adequately clean a particular string of switches, then the entire string is removed and replaced.

It would be desirable to provide a sensing assembly for accurately detecting patient and patient table interference with a gantry so that the gantry can be remotely tilted and so that during a scan, the scan or tilt is not stopped unnecessarily due to a false detection. It also would be desirable for such assembly to be inexpensive and easy to install.

SUMMARY OF THE INVENTION

These and other objects may be attained with an interference detection assembly for a CT system which, in one embodiment, includes a frusto-conical capacitive plate secured to the leading frusto-conical surface of the gantry bore. The capacitive plate is coupled to a control unit which detects changes in the capacitance between the capacitive plate and a patient or patient table, i.e., the capacitance of the plate. When the capacitance of the plate is outside a predetermined range, the control unit generates a signal which may be used to automatically interrupt a scan.

In operation, and as an operator remotely causes the gantry to tilt, if the patient and patient table come into close proximity to the plate, the voltage stored on the plate will change. Particularly, since the patient and the patient table are grounded, if the patient or patient table comes into close proximity with the plate, the voltage of the plate will begin to change. By detecting this change in capacitance, i.e., the change in voltage, the patient table and gantry movement can be immediately interrupted before any physical contact occurs.

Further, the capacitive plate is not as susceptible to erroneously indicating interference because items such as sheets do not significantly affect the dielectric of the capacitor formed by the plate and ground. Grounded objects such as the patient table, or the patient, however, cause such a change even before contact is made. The capacitive plate also is extremely easy to clean.

In another embodiment, the interference detection assembly includes an optic fiber wrapped in a fine polymer wire and secured to the leading frusto-conical surface of the gantry bore. The fiber is wrapped so that one surface of the fine polymer wire is adhesively secured to the leading gantry surface. A light source is coupled to the fiber and inputs light pulses into one end of the fiber. An opto-electric interface unit is secured to the other end of the optic fiber and detects the transmitted pulses. This assembly operates as a pressure sensor in that if physical contact is made with the wrapped wire, the wire deforms the optic fiber which results in distorting the light pulses being transmitted through the fiber. Such distortion is detected by the opto-electric interface unit, and upon detection of such distortion, the unit generates a signal which may be used to automatically interrupt a scan.

As with the capacitive plate, the above-described optic fiber wrapped in fine polymer wire is easy to clean. In addition, the optic fiber assembly is not likely to erroneously indicate interference.

DETAILED DESCRIPTION OF THE DRAWINGS

Figure 1:
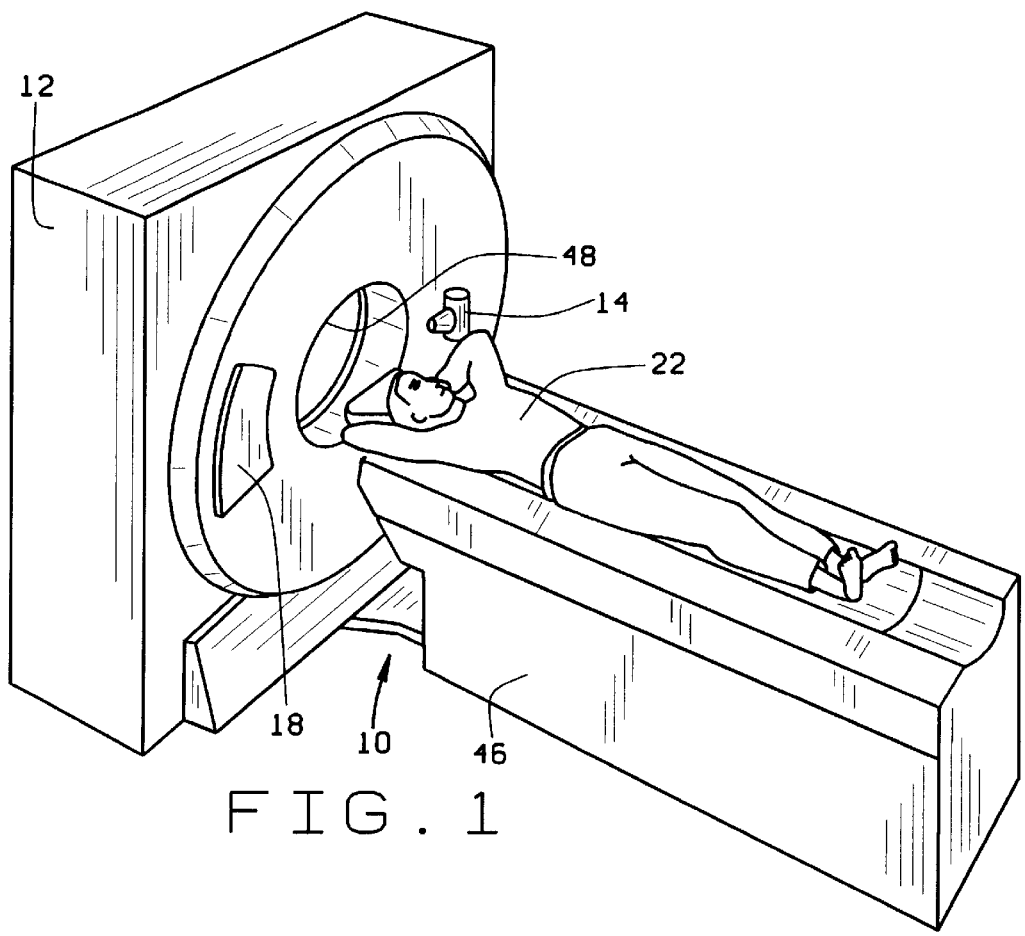
FIG. 1 is a pictorial view of a CT imaging system.
Figure 2:
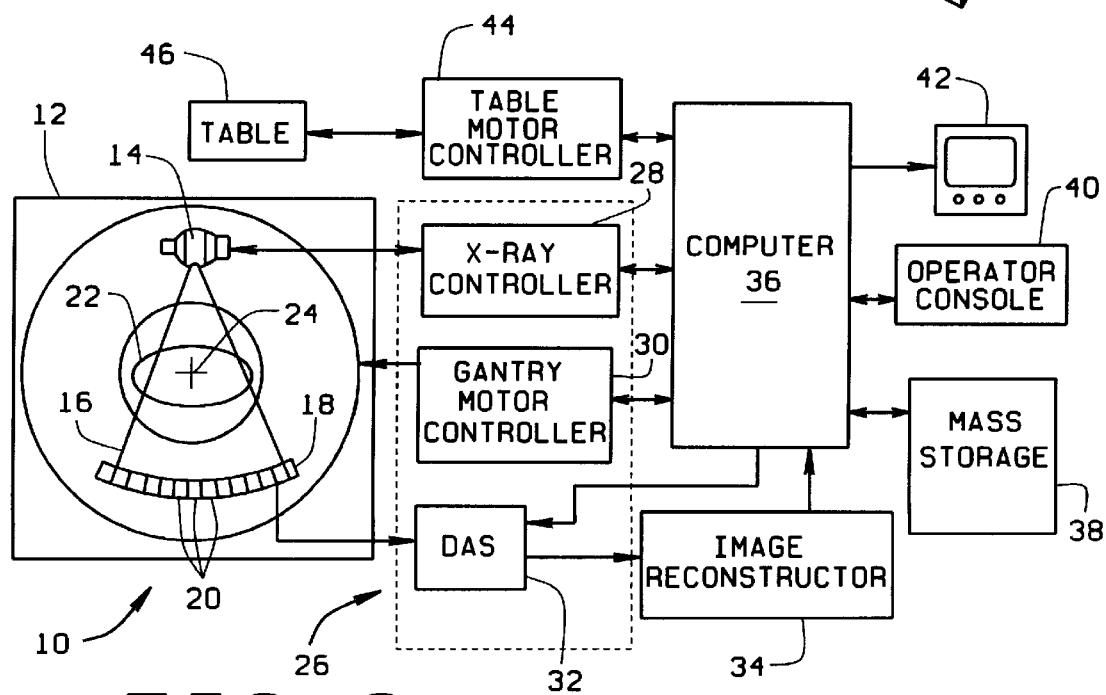
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46, or patient table, to position patient 22 in gantry 12. Particularly, table 46 moves portions of patient 22 through gantry opening 48. Gantry opening 48 is sometimes referred to herein as the gantry bore.

The following discussion of interference detection sometimes refers specifically to CT scanners, which typically include gantry bores having a leading frusto-conical section. The interference detection assembly, however, is not limited to practice in connection with only such gantries, and may be used with other gantries having different gantry bore configurations.

Figure 3:
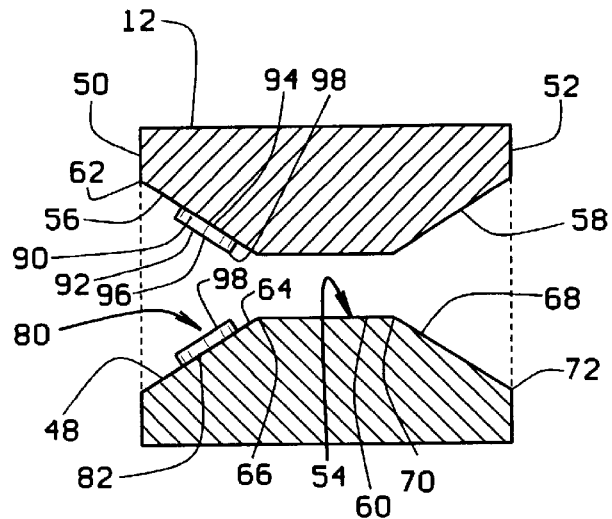
FIG. 3 is a partial cross-sectional view, with parts cut away, of the gantry shown in FIG. 1 including an interference detector in accordance with one embodiment of the present invention.

FIG. 3 is a partial cross-sectional view, with parts cut away, of gantry 12. Gantry 12 includes a first end 50 and a second end 52. First end 50 of gantry 12 includes gantry opening 48, and a gantry bore 54 extends from gantry opening 48 between first and second ends 50 and 52. Gantry bore 54 includes a substantially frusto-conical leading surface 56, an substantially frusto-conical exit surface 58, and a substantially cylindrical intermediate surface 60 between frusto-conical surfaces 56 and 58. More specifically, leading surface 56 of bore 54 tapers from a large perimeter 62 adjacent first end 50 of gantry 12 to a small perimeter 64 at an interface 66 between leading surface 56 and intermediate surface 60. Conversely, bore exit surface 58 increases from a small perimeter 68 at an interface 70 with intermediate surface 60 to a large perimeter 72 adjacent second end 52 of gantry 12.

In accordance with one embodiment of the present invention, an interference detection assembly 80 detects possible patient 22 and patient table 46 interference with gantry 12 and generates a signal representative of such interference. Interference detection assembly 80 includes an interference detector 82 which is secured to leading surface 56 of gantry bore 54 and a control unit (not shown) for generating a signal when possible gantry interference is detected. The control unit is electrically coupled to gantry 12 and table 46 so that gantry 12 rotation and table 46 movement are interrupted if possible interference is detected. For example, computer 36 may coupled to the signal unit to receive signals from the control unit, and to halt table 46 movement and gantry 12 rotation upon receipt of a signal from the control unit. Many other alternative implementations are, of course, possible.

In one form, interference detection assembly 80 includes a capacitive plate 90. Capacitive plate 90 is substantially frusto-conical and includes an opening 92 extending axially therethrough. Capacitive plate 90 includes a mounting surface 94 and a detecting surface 96. Mounting surface 94 is secured (e.g., by an epoxy adhesive) to leading surface 56 of bore 54, and detecting surface 96 is substantially parallel to leading surface 56. Particularly, capacitive plate 90 is secured to leading surface 56 of bore 54 so that capacitive plate 90 is positioned between interface 66 and large perimeter 62 of leading surface 56. Accordingly, a perimeter 98 of plate opening 92 is adjacent interface 66. As shown in FIG. 3, plate opening perimeter 98 is spaced from interface 66 so that mounting surface 94 of plate 90 is substantially flush with leading surface 56 of bore 54. In one form, plate 90 is located on the inside of gantry cover (not shown).

Capacitive plate 90 is coupled to a control unit (not shown) which detects changes in the capacitance of capacitive plate 90 i.e., changes in the capacitance formed by capacitive plate 90 and an external object such as patient 22 or table 46. The control unit is configured to activate, i.e., generate an interference signal, in response to a change in such capacitance. Particularly, the control unit is configured to detect a change in a dielectric constant adjacent detecting surface 96 of capacitive plate 90 caused by patient 22, or patient table 46, moving into close proximity with capacitive plate 90. Change in the capacitance of plate 90 may be determined, for example, with an AC Wheatstone Bridge. Alternatively, such a change may be determined either by measuring voltage on plate 90, by utilizing known tuning methods, or by using a resonant point of an L-C circuit. The control unit generates a signal representative of interference with gantry 12 when the capacitance changes between capacitive plate 90 and patient 22 or patient table 46 because of patient 22 or table 46 being in close proximity with capacitive plate 90.

Figure 4:
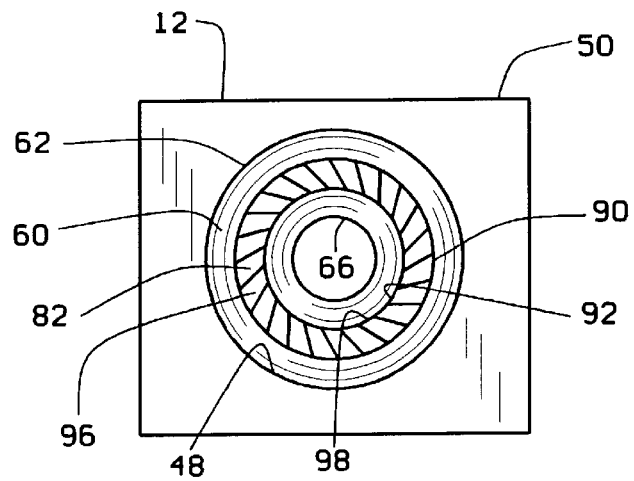
FIG. 4 is a partial front elevation view of the gantry and the capacitive plate shown in FIG. 3.

FIG. 4 is a partial front elevation view of gantry 12 and capacitive plate 90. Capacitive plate 90 has a substantially circular cross-sectional geometric shape with opening 92 adjacent interface 66. As shown, capacitive plate 90 is positioned between large perimeter 62 of leading surface 56 of gantry bore 54 and interface 66. More specifically, capacitive plate 90 is positioned so that capacitive plate is spaced from both larger perimeter 62 and interface 66.

In operation and prior to scanning patient 22, capacitive plate 90 is charged using well known charging techniques. While performing the scan, patient 22 and table 46 are translated, or moved, through gantry bore 54 and gantry 12 is rotated about the translating table 46. To obtain different views, an operator may remotely tilt gantry 12, for example, via input console 40. If, while tilting gantry 12, table 46 or patient 22 comes into close proximity to capacitive plate 90, then the capacitance of capacitive plate 90 i.e., in capacitive between capacitive plate 90 and patient 22 or table 46, changes. Particularly, and because patient 22 and table 46 are grounded, approaching patient 22 and table 46 cause a change in capacitance even without physically contacting capacitive plate 90. When the capacitance between capacitive plate 90 and patient 22 or table 46 has changed to a threshold value, the control unit generates a signal representative of interference with gantry 12. The signal may, as described above, be transmitted to computer 36 to interrupt gantry tilting and table movement. Essentially, the patient 22 or table 46 operates as a second plate of a two plate capacitor.

The above-described interference detection assembly 80 facilitates accurate detection of patient 22 and patient table 46 interference with gantry 12. Moreover, the interference is detected before patient 22 or table 46 physically contact capacitive plate 90. Of course, many modifications can be made to assembly 80. For example, and rather than one frusto-conical capacitive plate, the detection assembly may include two semi-frusto-conical capacitive plates. Similarly, the detection assembly may include a plurality of non-frusto-conical capacitive plates. In addition, computer 36 may include a processor which is coupled to the control unit.

Furthermore, and in accordance with another embodiment of the present invention, detection assembly 80 includes a second capacitive plate (not shown) which is secured to exit gantry bore surface 58 to detect gantry interference at exit surface 58. The second capacitive plate is coupled to a second control unit which detects changes in capacitance formed by the second capacitive plate and patient 22 or table 46. The second capacitive plate and control unit are configured the same as described above with respect to capacitive plate 90 and the control unit coupled to capacitive plate 90. Moveover, the second capacitive plate and second control unit operate the same way as described above with respect to capacitive plate 90 to generate a signal representative of interference with gantry 12. Accordingly, gantry interference may be detected with respect to both entry and exit bore surfaces 56 and 58, respectively.

Figure 5:
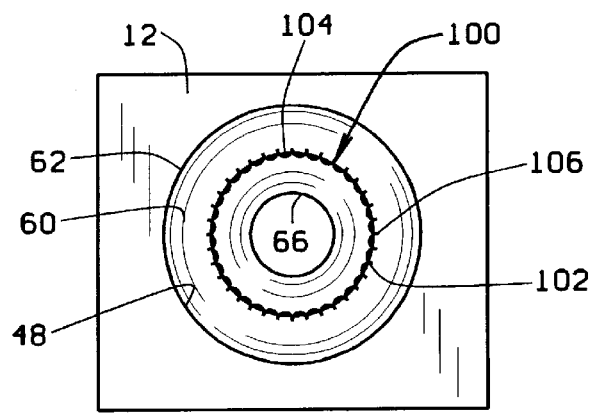
FIG. 5 is a partial front elevation view of the gantry shown in FIG. 1 and an interference detector in accordance with another embodiment of the present invention.

FIG. 5 is a partial front elevation view of gantry 12 and a detection assembly 100 in accordance with another embodiment of the present invention. Detection assembly 100 includes a fiber optic pressure sensor 102 having an optic fiber 104, an opto-electric interface unit (not shown), and a light emitter (not shown). Light emitters and opto-electric interface units are well known. Optic fiber 104 is wrapped (e.g., spiral wrapped) in a fine polymer wire 106, i.e., an external wire, and is coupled to both the light emitter and the opto-electric interface unit. Specifically, the light emitter is coupled to one end of (not shown) of optic fiber 104 and the opto-electric interface unit is coupled to the other end (not shown) of optic fiber 104.

Optic fiber 104 is secured to leading surface 56 of gantry bore 54 so that optic fiber 104 is concentric with the axis extending through gantry bore 54. Particularly, optic fiber 104 is configured in a circular geometry and secured to leading surface 56 of bore 54. The light emitter transmits light signals, or pulses, through optic fiber 104. The opto-electric interface unit receives pulses transmitted through optic fiber 104 and compares the received pulses to an expected signal value.

A second fiber optic sensor (not shown) similarly is secured to exit surface 58 of gantry bore 54. Particularly, a second optic fiber wrapped in a second external wire is secured to exit surface 58 so that the second optic fiber is concentric with the axis extending through gantry bore 54. A second light emitter is coupled to one end of the second optic fiber, and a second opto-electric interface unit is coupled to the other end of the second optic fiber. As described above, the light emitter transmits light signals, or pulses, through the second optic fiber. The opto-electric interface unit receives pulses transmitted through the second optic fiber and compares the received pulses to an expected signal value.

In operation, and referring solely to fiber optic fiber 104, detection assembly 100 operates as a pressure sensor in that if patient 22 or table 46 physically contacts external wire 106, then external wire 106 deforms, e.g., compresses, optic fiber 104 and distorts the light pulses transmitted by the light emitter through optic fiber 104. The opto-electric interface unit, upon detecting such distortion, generates an interference signal and transmits such signal to, for example, computer 36 to interrupt the scan. The second fiber optic pressure sensor detects interference in the same manner.

The above-described detection assemblies each provide adequate interference detection while using only one detection unit, e.g., one capacitor plate or one optic fiber. In addition, such detection assemblies are believed to be more accurate than tape switches and other sensors current used in CT systems. Furthermore, such detection assemblies generate signals representative of interference with the gantry, and thus facilitate tilting the gantry from a remote location.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. An interference detection assembly for a computed tomography system, the system including a gantry and a patient table, the gantry including a first end, a second end, and a gantry bore extending between the first end and the second end, the gantry bore including a frustro-conical leading surface, said assembly comprising at least one capacitive plate secured to the leading surface of the gantry bore.

2. An interference detection assembly in accordance with claim 1 further including a control unit coupled to said capacitive plate.

3. An interference detection assembly in accordance with claim 2 wherein said control unit is configured to detect a change in capacitance of said capacitive plate.

4. An interference detection assembly in accordance with claim 3 wherein said control unit is further configured to generate a signal representative of interference with the gantry.

5. An interference detection assembly in accordance with claim 1 wherein said capacitive plate has a substantially circular cross-sectional geometric shape.

6. An interference detection assembly in accordance with claim 1 wherein said capacitive plate has a substantially frusto-conical geometry.

7. An interference detection assembly in accordance with claim 6 comprising one capacitive plate.

8. An interference detection assembly in accordance with claim 1 wherein the gantry bore further includes a frusto-conical exit surface, and wherein said assembly further comprises a capacitive plate secured to the exit frusto-conical surface.

9. An interference detection assembly for a computed tomography system, the system including a gantry and a patient table, the gantry including a first end, a second end, and a gantry bore extending between the first end and the second end, the gantry bore including a frustro-conical leading surface, said assembly comprising at least one wire wrapped optic fiber secured to the leading surface of the gantry bore.

10. An interference detection assembly in accordance with claim 9 wherein said optic fiber is secured to the surface of the gantry bore so that said optic fiber is concentric with an axis extending through the gantry bore.

11. An interference detection assembly in accordance with claim 9 further comprising an opto-electric interface unit and a light emitter, said light emitter coupled to one end of said optic fiber, said opto-electric interface unit coupled to the other end of said optic fiber.

12. An interference detection assembly in accordance with claim 11 wherein said opto-electric interface unit is configured to generate a signal representative of interference with the gantry.

13. An interference detection assembly in accordance with claim 9 wherein the gantry bore includes a substantially frusto-conical section having a substantially frusto-conical surface, and said optic fiber is secured to said frusto-conical surface.

14. An interference detection assembly in accordance with claim 9 wherein said optic fiber is wrapped in a fine polymer wire.

15. An interference detection assembly in accordance with claim 9 wherein the gantry bore further includes an exit frusto-conical surface, and wherein said assembly further comprises a wire wrapped optic fiber secured to the exit frusto-conical surface.

* * * * *